United States Patent [19]

Dressaire et al.

[11] Patent Number: 5,426,239
[45] Date of Patent: Jun. 20, 1995

[54] CONTINUOUS PROCESS FOR THE INDUSTRIAL MANUFACTURE OF DIMETHOXYETHANAL

[75] Inventors: Gilles Dressaire, Trosly Breuil; Alain Schouteeten, Ezanville, both of France

[73] Assignee: Societe Francaise Hoechst, Puteaux, France

[21] Appl. No.: 181,306

[22] Filed: Jan. 13, 1994

[30] Foreign Application Priority Data

Jan. 19, 1993 [FR] France ................. 93 00470

[51] Int. Cl.$^6$ .............. C07C 41/01; C07C 43/04; C07C 47/193; C07C 45/04
[52] U.S. Cl. ................... 568/465; 568/486
[58] Field of Search .......................... 568/465

[56] References Cited

U.S. PATENT DOCUMENTS 2,288,211 6/1942 Schulz ............................ 568/465

FOREIGN PATENT DOCUMENTS 0249530 12/1987 European Pat. Off. .

OTHER PUBLICATIONS

Stambouli, A. et al. "Les dialkoxy -2,2 éthanals, synthons difonctionnels à deux carbones: preéparation par acétalisation du glyoxal et quelques applications en synthése."0 Bulletin De La Society Chimque De France. No. 1 (1988: Paris, France). pp. 95–100.

*Primary Examiner*—Joseph E. Evans
*Attorney, Agent, or Firm*—Browdy and Neimark

[57] ABSTRACT

Process for the continuous preparation of dimethoxy ethanal (DME) in which a 70% by weight of an aqueous solution of glyoxal is continuously reacted with 8 to 12 moles of methanol/mole of glyoxal in the presence of a cation exchange resin, then the reaction solution obtained is subjected to an initial distillation, at atmospheric pressure, in order to recover more than 90% of the unreacted methanol, which is recycled, then to a second distillation under a pressure of less than 10±2 kPa in order to isolate an aqueous mixture containing the greater part of DME and 1,1,2,2-tetramethoxyethane (TME) formed. This mixture, after dilution with water (molar ratio of water/TME 29±4), is subjected to a distillation under a pressure of less than 19 kPa in order to remove from the top fraction an aqueous mixture containing more than 98.5% of the TME present and to also obtain an aqueous solution of DME having a purity greater than 98.5%, and that, at the same time as these operations, the aqueous mixture containing the TME as well as the bottom fraction of the distillation produced from the distillation column of aqueous mixture containing the greater part of DME and TME, is treated continuously while warm, in the presence of a cation exchange resin, in order to obtain a water-methanol-glyoxal mixture, the methanol of which is evaporated off and recycled with the methanol recovered previously, before recycling half of it with the starting aqueous glyoxal solution after having been concentrated and recycling half with the aqueous mixture containing the TME.

6 Claims, No Drawings

CONTINUOUS PROCESS FOR THE INDUSTRIAL MANUFACTURE OF DIMETHOXYETHANAL

The present invention relates to a continuous process for the industrial manufacture of dimethoxy ethanal.

Dimethoxy ethanal, designated hereinafter as DME, is a synthesis product (synthon) of formyl olefination known to allow access to products endowed with useful physiological or aromatic properties (E. J. COREY et al, J. Amer. Chem. Soc., 1988, 110, 649–650; A. STAMBOULI et al, Tetrahedron Letters, 1987, 27, 5301–02; U.S. Pat. Nos. 4,171,318 and 4,011,233; Swiss Patent No. 590,857; German Patent No. 2,418,142; European Patent No. 0,246,646).

In particular, DME can be prepared by reducing acrolein dimethyl acetal ozonide (European Patent Application No. 0,146,784), either by the oxidizing cleavage of dihydroxy-2,3-tetramethoxy-1,1,4,4 butane (L. A. YANOVSKAYA et al, Izv. Akad. Nauk SSSR, Otd. Khim Nauk, 1963, 857–65), or by carefully hydrolyzing acetoxy-1-trimethoxy-1,2,2 ethane (A. STAMBOULI et al, Tetrahedron Letters, 1986, 26, 4149–52), or by the monoacetalization of glyoxal (European Patent Application No. 0,249,530, A. STAMBOULI et al, Bull Soc. Chim. France, 1988, 95–100, and H. SANGSARI et al, Synthetic Comm. 1988, 18, 1343). These processes are however difficult to put into operation for the industrial production of large quantities due to the fact they are dangerous (risk of explosion of the acrolein dimethyl acetal ozonide, cf. German Patent Application No.: 2,514,001), are costly due to the use of expensive raw materials or to the need to carry out delicate purification by distillation at the end of the reaction.

In order to overcome these disadvantages, the Applicant has disclosed a continuous industrial process for the preparation of DME starting from glyoxal in aqueous solution.

According to the invention, an aqueous solution containing more than 60% by weight of DME, with a purity in excess of 98.5% is continuously obtained with an almost quantitative yield relative to the glyoxal used by a process characterized in that an approximately 70% by weight aqueous solution of glyoxal is continuously reacted with 8 to 12 moles of methanol per mole of glyoxal used, in the presence of a cation exchange resin having sulphonic groups in acid form, then the neutral reaction solution obtained, containing less than 1.5% glyoxal by weight is subjected to an initial distillation, at atmospheric pressure, in order to recover more than 90% of the unreacted methanol, which is recycled, then to a second distillation under a pressure of less than $10\pm2$ kPa in order to isolate an aqueous mixture containing the greater part of DME and 1,1,2,2-tetramethoxyethane formed (hereinafter called TME), that this mixture, after dilution with water in a manner such that the molar ratio of water to TME is $29\pm4$, is subjected to a distillation under a pressure of less than 19 kPa in order to eliminate, from the top fractions an aqueous mixture containing more than 98.5% of the TME present and to also obtain an aqueous solution of DME having a purity greater than 98.5%, which, if desired, is concentrated under reduced pressure in order to obtain the required concentration of DME, and that, at the same time as these operations, the aqueous mixture containing the TME as well as the bottom fraction of the distillation produced from the distillation column of the aqueous mixture containing the greater part of the DME and the TME is treated continuously while warm in the presence of a cation exchange resin having sulphonic groups in acid form, in order to obtain a water-methanol-glyoxal mixture, the methanol of which is evaporated off and recycled with the methanol recovered previously, before half is recycled with the starting aqueous glyoxal solution, after having adjusted its concentration of glyoxal to approximately 70% by weight by evaporation under reduced pressure, and half is recycled with the aqueous mixture containing the TME.

In the preferred conditions for implementing the invention, the continuous process described below is carried out in the following way:

A) The reaction of glyoxal with the methanol is carried out continuously at atmospheric pressure:
in a column thermostatically-controlled at a temperature of $60°\pm5°$ C.;
by percolating approximately one mmole of glyoxal in aqueous solution for x hours and per y ml of a cation exchange resin having sulphonic groups in acid form, having an exchange capacity of $3\pm2$ meq/ml, x and y being two positive numbers, less than 10 such that $xy=1$, advantageously $x=y=1$.

B) The purification of the solution is carried out:
continuously, at neutral pH;
by, in the first place, isolating the unreacted methanol by evaporation, which is then recycled, then by distillation under a pressure of less than $10\pm2$ kPa and at a temperature of approximately 75° C., more than 75% by weight of DME and of TME formed as a mixture with the water and the residual methanol and simultaneously recovering the unreacted glyoxal from the bottom fraction of the distillation as well as the residual DME and the TME;
by diluting the above distillate containing the larger proportion of the DME formed with the water in a manner such that the molar ratio of water to TME is approximately $29\pm1$, then by subjecting it to a distillation under reduced pressure, at a temperature of less than $70\pm5°$ C., in order to recover 99 $\pm1\%$ of the TME present as a mixture with water and the residual methanol;
by isolating the TME formed in the form of an aqueous mixture containing approximately 50 to 75% water by weight;
by decomposing while hot, in the presence of a cation exchange resin having sulphonic groups in acid form, the TME in aqueous solution isolated previously in a water-methanol-glyoxal mixture, the methanol of which is separated out by evaporation, which is then recycled, then, on half of the residual solution, water in excess is separated out in such a way as to obtain an approximately 70% by weight aqueous glyoxal solution, which is also recycled, the other half being recycled in the decomposition medium;
by carrying out the preceding decomposition in a column identical to that used to carry out the reaction of glyoxal with methanol, thermostatically-controlled at a temperature of 80° C. $\pm5°$ C. and filled with the same quantity of the same cation exchange resin;
by introducing into the TME decomposition column on the one hand the bottom fraction of the distillation containing the unreacted glyoxal as well as the residual DME and TME and on the other hand, half the hydrolysis medium produced from this decomposition after recovering by evaporation the methanol formed.

The pure DME can be isolated from its aqueous solution by evaporation of the water under reduced pressure optionally in the presence of a third organic solvent giving an azeotrope with water followed, if desired, by distillation under reduced pressure. DME is an easily polymerisable colourless liquid, distilling at 59°±2° C. under a pressure of 5.3±0.3 kPa.

The following example illustrates the present invention without however limiting it. Unless indicated otherwise, the percentages given are percentages by weight.

EXAMPLE 1

In a column R1, equipped with a double casing, 80 cm in diameter and 250 cm in length, thermostatically-controlled at 60° C. ±3° C. by warm water circulating in the outer casing and containing 1000 l of a cation exchange resin with sulphonic groups in acid form, with an exchange capacity of 3±2 meq/ml, 467 kg/h of a mixture is circulated at atmospheric pressure and at constant speed, containing in molar proportions 83.45% methanol, 9.60% of water and of 6.95% glyoxal. On leaving the column, the neutral reaction solution, containing less than 1.5of unreacted glyoxal by weight is distilled in a column C1 in order to recover approximately 92% of the methanol present, which is collected by mixing with 2 to 5% water, then it is distilled under a pressure of 11 kPa, in an evaporator C2 where the top fractions containing the glyoxal acetals, the residual methanol and less than 0.05% of the glyoxal are collected which, after continuous distillation with 125±30 kg/h of water are distilled again under a pressure of 17 kPa in a column C3 where, from the top of the column an aqueous mixture is collected containing the methanol and approximately 99% of the residual TME, and from the bottom of the column, 430 moles/h of DME with a purity greater than 98.75% in aqueous solution, which, if desired, can be concentrated in a column C4 in order to obtain an aqueous solution containing 70% of DME having a purity in excess of 98.75%.

The fractions from the top of the column C3 are continuously mixed, on the one hand, with the bottom of the column C2 and on the other hand with 50% of the bottom of the column C5 given below, then the mixture is sent into a column R2, identical with column R1, containing the same quantity of the same cation exchange resin in acid form and thermostatically-controlled at 85°±2° C. by circulating warm water. On leaving column R2, a mixture containing only water, glyoxal and methanol is obtained, which is distilled in column C5 in order to separate from the top of the column more than 99% of the methanol present as a mixture with 1 to 5% of water and from the bottom of the column a mixture of glyoxal and water, half of which is recycled in column R2 and half of which is recycled in column R1, after having been concentrated in a column C6 in order to obtain a 70% aqueous solution of glyoxal; approximately 565 moles/h of glyoxal are recycled in this way. The methanol-water mixtures collected from the top of columns C1 and C5 are combined, then distilled in a column C7 where approximately 11.1 kmole/h of methanol are collected from the top of the column, which are recycled in column R1. In this way, DME with a purity greater than 98.75% in aqueous solution is contained continuously with a yield greater than 99% relative to the glyoxal used.

In continuous operation, column C6 is supplied with approximately 63 kg/h of a 40% by weight glyoxal aqueous solution, that is about 434 moles/h, and column C7 is supplied with approximately 29 kg/h (905 moles/h) of methanol and approximately 430 moles/h of DME in aqueous solution are obtained, which can either be diluted with water, or concentrated under reduced pressure, in order to obtain the desired concentration of DME.

We claim:

1. Process for the continuous preparation of dimethoxy ethanal characterized in that a 70% by weight aqueous solution of glyoxal is continuously reacted in a column R1 with 8 to 12 moles of methanol per mole of glyoxal used, in the presence of a cation exchange resin having sulphonic groups in acid form, then the neutral reaction solution obtained, containing less than 1.5% of glyoxal by weight, is subjected to an initial distillation in a column C1, at atmospheric pressure, in order to recover more than 90% of the unreacted methanol, which is recycled, then to a second distillation in a column C2 under a pressure of less than 10±2 kPa in order to isolate as overhead an aqueous mixture containing the greater part of dimethoxy ethanal and 1,1,2,2-tetramethoxyethane formed, that this mixture, after dilution with water in a manner such that the molar ratio of water to 1,1,2,2-tetramethoxyethane is 29±4, is subjected to a distillation in a column C3 under a pressure of less than 19 kPa in order to eliminate, from the top fractions, an aqueous mixture containing more than 98.5% of the tetramethoxy-1,1,2,2-ethane present and to also obtain as bottoms an aqueous solution of dimethoxy ethanal having a purity greater than 98.5%, which, if desired, is concentrated under reduced pressure in order to obtain the required concentration of dimethoxy ethanal, and that, at the same time as these operations the aqueous overhead mixture from C3 containing the 1,1,2,2-tetramethoxyethane as well as the bottom fraction from C2 of the distillation produced from the distillation column of the aqueous mixture containing the greater part of the dimethoxy ethanal and the 1,1,2,2-tetramethoxyethane is treated continuously in a column R2 while warm in the presence of a cation exchange resin having sulphonic groups in acid form, in order to obtain a water-methanol-glyoxal mixture, the methanol of which is evaporated off in a column C5 and recycled with the methanol recovered previously, before half of the nonevaporated water and glyoxal is recycled with the starting aqueous glyoxal solution, after having adjusted its concentration of glyoxal to approximately 70% by weight by evaporation under reduced pressure, and the other half is recycled to R2 with the aqueous mixture containing the 1,1,2,2-tetramethoxyethane from the overhead from C3.

2. Process according to claim 1, characterized in that the reaction in R1 is carried out by percolating one mmole of glyoxal in aqueous solution, per x hours and per y ml of a cation exchange resin, having sulphonic groups, in acid form, having an exchange capacity of 3±2 meq/ml, x and y representing two positive numbers, lower than 10 such that xy=1.

3. Process according to claim 1 characterized in that the reaction in R1 is carried out by percolating in the presence of 1 ml of a cation exchange resin, having sulphonic groups, in acid form, having an exchange capacity of 3±2 meq/ml, per hour and per mmole of glyoxal used.

4. Process according to claim 1 characterized in that the reaction of glyoxal in aqueous solution with the methanol is effected at a temperature of 60°±5° C.

5. Process according to claim 2 characterized in that the reaction in R1 is carried out by percolating in the presence of 1 ml of a cation exchange resin, having sulphonic groups, in acid form, having an exchange capacity of 3±2 meq/ml, per hour and per mmole of glyoxal used.

6. Process according to claim 5, characterized in that the reaction of glyoxal in aqueous solution with methanol is effected at a temperature of 60°±5° C.

* * * * *